United States Patent
D'Onofrio et al.

(10) Patent No.: US 11,015,983 B2
(45) Date of Patent: May 25, 2021

(54) INDICATOR OF STERILIZATION EFFICACY USING A DATA LOGGER WITH CLOUD/SOFTWARE APPLICATION

(71) Applicant: Maxim Integrated Products, Inc., San Jose, CA (US)

(72) Inventors: Michael James D'Onofrio, Dallas, TX (US); Carlos Manuel Contreras, Denton, TX (US); Raghunath Puttaiah, Plano, TX (US)

(73) Assignee: Maxim Integrated Products, Inc., San Jose, CA (US)

( * ) Notice: Subject to any disclaimer, the term of this patent is extended or adjusted under 35 U.S.C. 154(b) by 439 days.

(21) Appl. No.: 15/778,133

(22) PCT Filed: Nov. 14, 2016

(86) PCT No.: PCT/US2016/061788
§ 371 (c)(1),
(2) Date: May 22, 2018

(87) PCT Pub. No.: WO2017/095612
PCT Pub. Date: Jun. 8, 2017

(65) Prior Publication Data
US 2018/0348061 A1    Dec. 6, 2018

Related U.S. Application Data

(60) Provisional application No. 62/261,782, filed on Dec. 1, 2015, provisional application No. 62/261,749, filed
(Continued)

(51) Int. Cl.
*G01K 1/02*    (2021.01)
*G01K 1/022*   (2021.01)
(Continued)

(52) U.S. Cl.
CPC .............. *G01K 1/022* (2013.01); *G01K 1/08* (2013.01); *G01K 7/42* (2013.01); *G01K 13/02* (2013.01); *G06F 11/3476* (2013.01); *A61L 2/28* (2013.01)

(58) Field of Classification Search
None
See application file for complete search history.

(56) References Cited

U.S. PATENT DOCUMENTS

| | | | |
|---|---|---|---|
| 10,668,177 B1 * | 6/2020 | D'Onofrio | G01M 99/008 |
| 2002/0029111 A1 * | 3/2002 | Peek | G01W 1/10 |
| | | | 702/3 |

(Continued)

FOREIGN PATENT DOCUMENTS

| | | | | |
|---|---|---|---|---|
| WO | WO 2017095612 | * | 6/2017 | G01K 13/02 |
| WO | WO 2017095612 A | * | 6/2017 | G01K 1/022 |

OTHER PUBLICATIONS

International Search Report dated Jan. 26, 2017, in International PCT Patent Application No. PCT/US2016/061788, filed Nov. 14, 2016 (2pgs).

(Continued)

*Primary Examiner* — Tung S Lau
(74) *Attorney, Agent, or Firm* — North Weber and Baugh LLP; Michael North

(57) ABSTRACT

The invention relates to a device (6) for communicating data with a data logger (28) that measures the temperature of ambient gas and logs the temperature data into a memory (55). The device (6) includes a body (73) for mounting a data logger (28) thereon, wherein the data logger (28) is disposed inside a capsule (12, 40). The data logger (28) includes: top and bottom covers (50, 51) that define an enclosed space and includes an electrical circuit (52) disposed in the enclosed space and having a memory (55) for storing data; a pair of electrodes (71, 72) for extending through two holes (18, 32)

(Continued)

formed in the capsule (12, 40) and contacting the top and bottom covers (50, 51) of the data logger, respectively; a processor (1001) for retrieving data stored in the memory (55) through the pair of electrodes (71, 72); and a communication device (1015) for transmitting the data.

20 Claims, 7 Drawing Sheets

Related U.S. Application Data on Dec. 1, 2015, provisional application No. 62/261,783, filed on Dec. 1, 2015.

(51) Int. Cl.
*G01K 7/42* (2006.01)
*G01K 1/08* (2021.01)
*G01K 13/02* (2021.01)
*G06F 11/34* (2006.01)
*A61L 2/28* (2006.01)

(56) References Cited

U.S. PATENT DOCUMENTS

| | | | | |
|---|---|---|---|---|
| 2007/0193297 A1* | 8/2007 | Wilson | ............... | F25D 29/00 62/371 |
| 2008/0089870 A1* | 4/2008 | Ghosh | ............... | C12N 5/0626 424/93.7 |
| 2008/0272131 A1* | 11/2008 | Roberts | ............... | G01K 1/14 220/592.25 |
| 2009/0030293 A1 | 1/2009 | Cooper et al. | | |
| 2010/0175393 A1* | 7/2010 | Burke | ............... | F25D 29/00 62/80 |
| 2010/0299278 A1 | 11/2010 | Kriss et al. | | |
| 2012/0092265 A1* | 4/2012 | Williams | ............... | G06F 1/1626 345/169 |
| 2012/0241443 A1* | 9/2012 | Tang | ............... | H05B 6/6441 219/679 |
| 2013/0197319 A1* | 8/2013 | Monty | ............... | A61B 10/0064 600/301 |
| 2013/0295153 A1* | 11/2013 | Miresmailli | ............... | A01M 1/2022 424/409 |
| 2013/0343734 A1* | 12/2013 | Dock, II | ............... | F24H 9/20 392/441 |
| 2014/0297229 A1* | 10/2014 | Izumo | ............... | G01D 9/00 702/189 |
| 2015/0018643 A1* | 1/2015 | Cole | ............... | A61B 5/14546 600/316 |
| 2015/0291327 A1* | 10/2015 | Cherukupalli | ............... | B32B 5/245 428/71 |
| 2016/0366330 A1* | 12/2016 | Boliek | ............... | G11B 27/36 |
| 2017/0284689 A1* | 10/2017 | Steele | ............... | E02D 29/12 |

OTHER PUBLICATIONS

Written Opinion dated Jan. 26, 2017, in International PCT Patent Application No. PCT/US2016/061788, filed Nov. 14, 2016 (4pgs).

\* cited by examiner

INDICATOR OF STERILIZATION EFFICACY USING A DATA LOGGER WITH CLOUD/SOFTWARE APPLICATION

CROSS REFERENCE TO RELATED PATENT APPLICATIONS

The present application is a U.S. 371 National Stage of PCT Patent Application No. PCT/US16/61788, entitled "INDICATOR OF STERILIZATION EFFICACY USING A DATA LOGGER WITH CLOUD/SOFTWARE APPLICATION," naming as inventors Michael James D'Onofrio, Carlos Manuel Contreras, and Raghunath Puttaiah, and filed Nov. 14, 2016, which claims priority benefit, under 35 U.S.C. § 119(e), to commonly assigned U.S. Provisional Patent Application No. 62/261,782, entitled "INDICATOR OF STERILIZATION EFFICACY USING A DATA LOGGER WITH CLOUD/SOFTWARE APPLICATION," naming as inventors Michael James D'Onofrio, Carlos Manuel Contreras, and Raghunath Puttaiah, U.S. Provisional Patent Application No. 62/261,749, entitled "APPARATUS FOR LOGGING DATA IN HARSH ENVIRONMENTS," naming as inventors Jeffery Alan Gordon, Scott Edward Jones, and Hal Kurkowski, and U.S. Provisional Patent Application No. 62/261,783, entitled "ALGORITHM TO CORRECT LAG BETWEEN INTERNAL TEMPERATURE SENSOR AND AMBIENT GAS," naming as inventors, Victor Levi, Michael James D'Onofrio, and Raghunath Puttaiah, which applications were filed Dec. 1, 2015, and which applications are hereby incorporated herein by reference in their entireties.

BACKGROUND

A. Technical Field

The present invention relates to systems and methods for monitoring sterilization cycles in harsh environments, and more particularly, to systems and methods for logging temperature data in harsh environments and processing the logged data.

B. Background of the Invention

Over the years, various devices for acquiring and storing temperature data have been developed to trace the history of ambient temperature surrounding the devices. Manufacturers and/or distributors send the device along with their products, such as drugs, that are sensitive to temperature changes, where the products need to remain within a preset temperature range to keep their original efficacy. The receivers of the products retrieve the temperature data stored in the device and check if the temperature of the products was outside the preset range during transportation.

In some applications, such as autoclave for steam sterilization, the ambient gas inside the autoclave may have the temperature of 140° C. and the pressure of 2 atmospheres, for instance. For each sterilization cycle, it may be necessary to determine whether the sterilization process is successful, i.e., it may be necessary to ensure that the correct sterilization parameters are reached to achieve the intended microbial kill. For instance, a user may set a parametric sterilization temperature and a parametric sterilization time and determine that the sterilization cycle is successful if the temperature of the ambient gas is maintained at the parametric sterilization temperature during the parametric sterilization time. FIG. 1 shows an exemplary plot 100 of temperature during a sterilization cycle. As depicted, the parametric sterilization temperature, Ts, is the preset sterilization temperature and the parametric sterilization time 102 is the time interval between the beginning point 104 and the end point 108 of the temperature plateau at Ts.

A conventional electronic device for logging temperature may be used to trace the ambient gas temperature during each cycle and the logged temperature data may be used to determine whether the sterilization cycle is successful. However, the capsule of the conventional device cannot prevent the ingress of moisture into the capsule, where the moisture damages the electronic components inside the capsule. As such, the conventional devices can survive only a few sterilization cycles at best and thus are not suitable for logging data during multiple cycles.

As such, in the conventional sterilization autoclave, a chemical indicator (integrator or emulator) is used to determine whether the process of the sterilization cycle is successful. The chemical indicator (CI) has a temperature sensitive strip that changes its color depending on the temperature and stay changed permanently. However, the chemical indicator may turn its color prematurely at a point in time 106 before the actual sterilization cycle is completed at the ending point 108. Thus, the conventional chemical indicator may not be able to indicate whether the parametric sterilization time 102 is reached.

In some cases, a conventional biological indicator (BI) is used to determine whether the sterilization cycle is successful (i.e., decide pass/fail of the cycle). The biological indicator is a paper strip filled with a preset number of *Geobacillus stearothermophilus* spores. Typically, a sterilization cycle is designed to achieve a 12 log reduction in spores half way through a cycle. However, in reality, they are all killed before a half cycle due to the stress of the temperature ramp up 107. Thus, the biological indicator may indicate the sterilization condition of the early portion of the cycle rather than the whole cycle. In addition, the biological indicator has a long turnaround time since the spore sample may need to be sent to a lab and, depending on the type of spores, incubation may be needed. Furthermore, the spore sample can be contaminated during the analyzing process.

Both the conventional CI and BI techniques require manual recording of paper logbooks, which is less efficient and more costly than electronic recording and processing of the data. Also, due to the high cost, both techniques are to be used for validation testing (per quarter or year) rather than for monitoring every cycle.

As such, there is a need for a device for electronically logging temperature data in harsh environments, where the data can be used to determine whether the preset sterilization condition is met during a sterilization cycle, to thereby decide pass/fail of the sterilization cycle.

SUMMARY OF THE DISCLOSURE

In one aspect of the present invention, a device for communicating data with a data logger includes a body for mounting a data logger thereon, wherein the data logger is disposed inside a capsule. The data logger includes: top and bottom covers that define an enclosed space and includes an electrical circuit disposed in the enclosed space and having a memory for storing data. The device further includes: a pair of electrodes for extending through two holes formed in the capsule and contacting the top and bottom covers of the data logger, respectively; a processor for retrieving data stored in the memory through the pair of electrodes; and a communication device for transmitting the data.

In another aspect of the present invention, a system for communicating data with a data logger includes: at least one processor; and a communication device that is communicatively coupled to the at least one processor and receives data from a data logger. The data logger is disposed inside a capsule that prevents ingress of atmospheric gas into the data logger. The data logger includes top and bottom covers that define an enclosed space and includes an electrical circuit disposed in the enclosed space and having a memory for storing the data.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Furthermore, connections illustrated in the figures between components may be modified or otherwise changed through the addition thereto of intermediary components, without departing from the teachings of the present invention.

Figure 2:
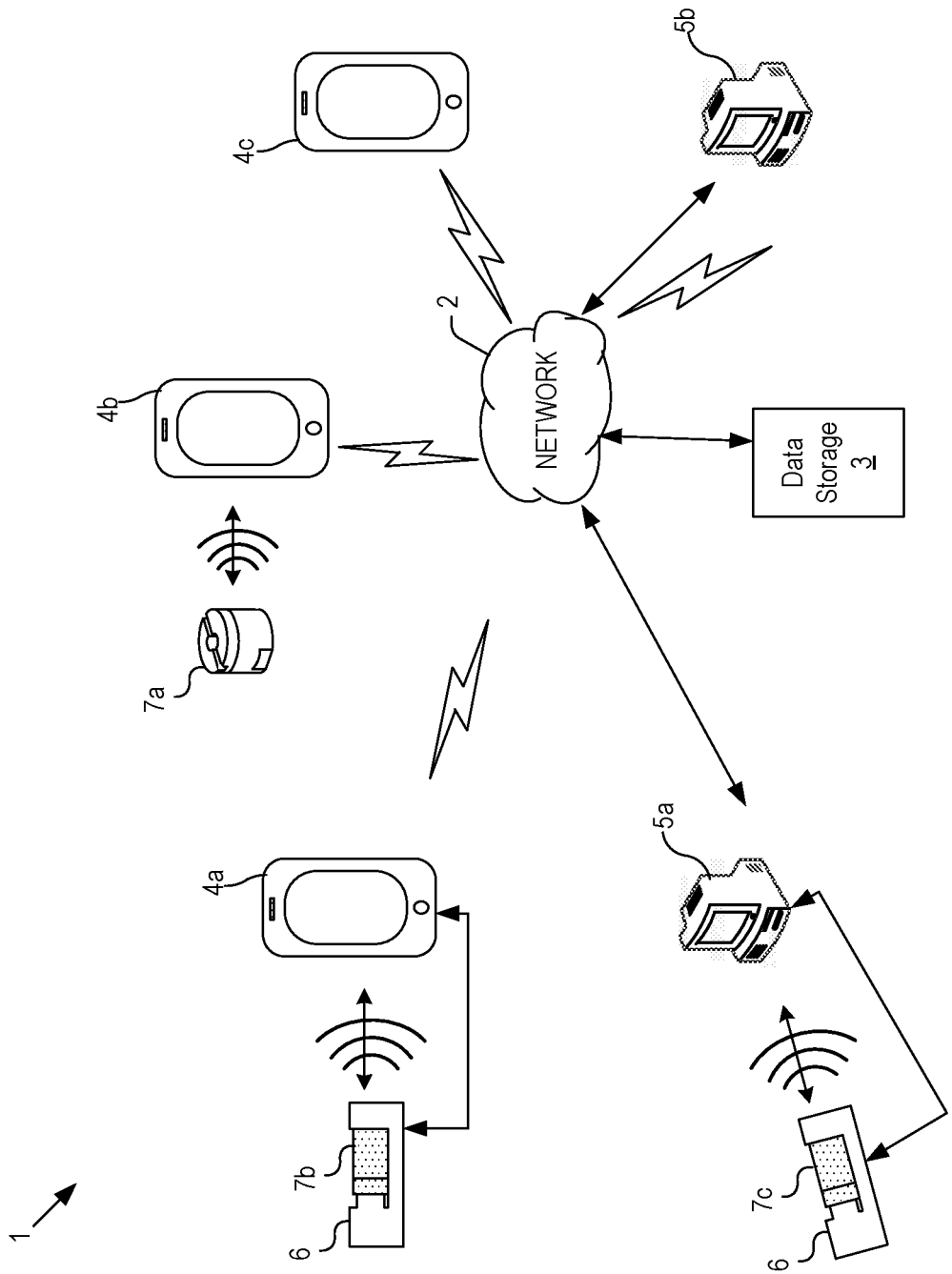
FIG. 2 shows a schematic diagram of an overall system for monitoring sterilization cycles according to embodiments of the present invention.

FIG. 2 shows a schematic diagram of an overall system 1 for monitoring sterilization cycles according to embodiments of the present invention. As indicated, data logging device (or, shortly data logger) 7a-7c may communicate data to various electronic devices, such as mobile devices 4a-4b and computer/server 5. As describe in conjunction with FIGS. 3A-9, each of the data logger 7a-7c may measure temperature of the ambient gas in an autoclave at a preset time and/or repeat measurements at a preset time interval, and store the measured data.

In embodiments, the data logger 7a may communicate wirelessly to the mobile device 4b. In embodiments, the data logger 7b and 7c have a capability to communicate to the mobile devices 4a or computer/server 5a via a reader 6. More detailed description of the reader 6 is given in conjunction with FIG. 8.

The mobile devices 4a-4c and computers/servers 5a-5b may communicate data to each other via a network 2, such as Internet. In embodiments, the mobile devices 4a-4c and computers/servers 5a-5b may store the temperature data into a data storage 3 so that a user may use the computer, e.g. 5b, to remotely access the data stored in the data storage 3. In embodiments, the data storage 3 may be Cloud storage. It is noted that other suitable computing devices may communicate to the data loggers 7a-7c and retrieve temperature data stored in the data loggers. It is also noted that other suitable number of mobile devices and/or computers/servers may be connected to the network 2.

Figure 3A:
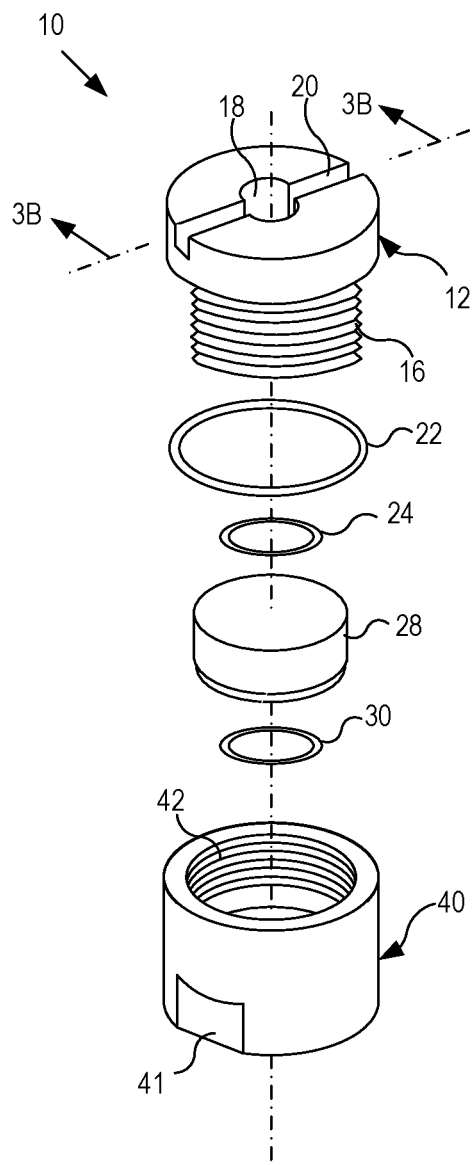
FIGS. 3A-3C show a package for logging temperature data according to one embodiment of the present invention.
Figure 3B:
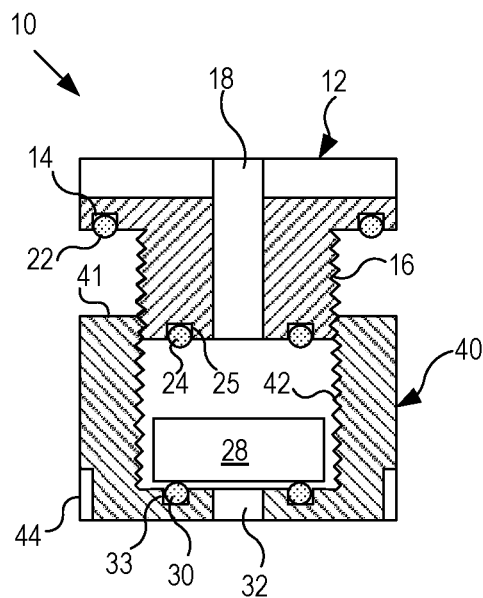
Figure 3C:
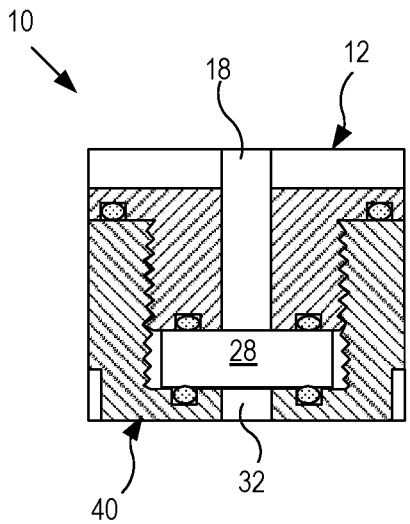

FIG. 3A shows an exploded view of a package 10 for logging temperature data according to one embodiment of the present invention. As depicted in FIG. 3A, the package 10 includes: a capsule having a plug 12, a base 40 and O-rings 22, 24, and 30; and a temperature data logger (or, shortly, data logger) 28 for logging temperature data under harsh environments. In embodiments, the data logger 28 may be an integrated circuit (IC)-based temperature data logger. FIG. 3B shows a cross sectional view of the package 10, taken along the direction 3B-3B, where the male thread 16 of the plug 12 is slightly engaged into the female thread 42 of the base 40. FIG. 3C shows the package 10, where the plug 12 is fully engaged into the base 40.

For the purpose of illustration, the package 10 is described as a temperature data logging device for a steam autoclave chamber, i.e., the package 10 is mounted inside a steam autoclave chamber and logs temperature data during sterilization cycles of the autoclave. For instance, an exemplary operational condition of the steam autoclave has the temperature of 140° C. and the pressure of 2 atmosphere, and each cycle may last 35-40 minutes, and the package 10 is designed to survive more than hundred cycles without being damaged by the ambient gas. However, it should be apparent to those of ordinary skill in the art that the package 10 may be applied to other test environments. Also, it should be apparent to those of ordinary skill in the art that the package 10 may be calibrated to accommodate different operational temperature ranges.

The plug 12 includes: a slot 20 for receiving a tool, such as torque wrench, for turning the plug 12 relative to the base

40; and a through hole 18 that allows the ambient gas to directly contact the top surface of the data logger 28 during operation. Since the ambient gas including hot steam is in direct contact with the data logger 28, the thermal lag between the chamber environment and the data logger 28 is reduced so that the data logger 28 can accurately track the temperature variation inside the chamber.

The O-rings 22, 24, and 30 are used to prevent ingress of moisture into the data logger 28. The O-ring 22 rests on a groove 14 that is formed on the plug 12. The O-ring 22 is compressed by the lip 41 of the base 40 when the plug 12 is fully engaged into the base 40, as shown in FIG. 3C, to thereby preventing ingress of the ambient gas through the gap between the male thread 16 and the female thread 42.

The O-rings 24 and 30 rest on grooves 25 and 33, respectively. When the package 10 is assembled, the O-rings 24 and 30 are compressed by the top and bottom surfaces of the data logger 28, respectively, to thereby prevent ingress of the ambient gas through the gaps between the capsule and the data logger 28.

The base 40 includes a through hole 32 that allows the ambient gas to directly contact the bottom surface of the data logger 28 during operation. Since the ambient gas is in direct contact with the data logger 28, the thermal lag between the chamber environment and the data logger 28 is reduced so that the data logger 28 can accurately track the temperature variation inside the chamber. The base 40 also includes a notch/recess 44 so that a proper device securely holds the base in place during assembly of the package 10.

If the package 10 is assembled while the O-rings 22, 24, and 30 are dry, the O-rings may not properly seal the space surrounding the data logger 28 due to pinching, crimping, or twisting of the O-rings. To avoid such deformation of the O-rings, small amount of grease is applied to the O-rings. The grease also holds the O-rings in their corresponding grooves temporarily during assembly. For instance, the O-rings 22 and 24 remain seated on the grooves 14 and 25, respectively, by the grease when the plug 12 is flipped over during assembly, as shown in FIG. 3B.

It is noted that the package 10 may be mounted in the autoclave chamber with other items, such as medical instruments, being sterilized. If the package 10 releases any toxic material into the autoclave chamber, the items may be contaminated by the toxic material. As such, all of the components, including the grease, of the package 10 are tested to ensure that none of the components release toxins during sterilization cycles.

The capsule is reusable, i.e., the user can disengage the male thread 16 from the female thread 42, replace the data logger 28, and reassemble the package 10. During this process, the user may not place one or more of the O-rings 22, 24 and 30 properly i.e., the user may misalign the O-rings on resealing. In embodiments, to obviate the improper reassembly by the user, a small amount of glue may be applied to the threads so that the plug and base are glued together.

Figure 4:
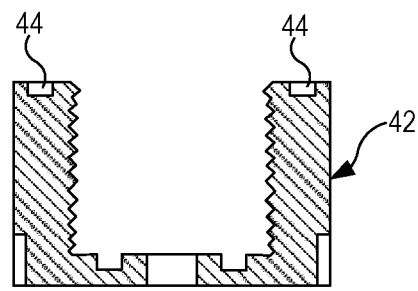
FIG. 4 shows a cross sectional view of a base of a capsule according to one embodiment of the present invention.

FIG. 4 shows a cross sectional view of a base 42 of a capsule according to one embodiment of the present invention. As depicted, the base 42 is similar to the base 40 in FIGS. 3A-3C, with the difference that the base 42 includes an O-ring groove 44 that the O-ring 22 rests on. It should be apparent to those of ordinary skill in the art that the package 10 may include other suitable types of sealing mechanisms to prevent the ingress of the ambient gas into the data logger 28.

The material for the plug 12 and base 40 (or 42) may be chosen for its mechanical properties (i.e., they remain stable during both long and short-term exposure to high temperature and pressure), inherent flame resistance, and outstanding chemical resistance (i.e., inert to high temperature steam, strong bases, fuels and acids). In embodiments, the plug and base are formed of a polymer, such as polyphenylene sulfide (PPS) Likewise, the material for the O-rings 22, 24, and 30 may be chosen for their mechanical strength and chemical qualities. In embodiments, the O-rings are formed of silicon, where the silicon O-rings are also resistant to sunlight, ozone, oxygen, and UV light.

Figure 5:
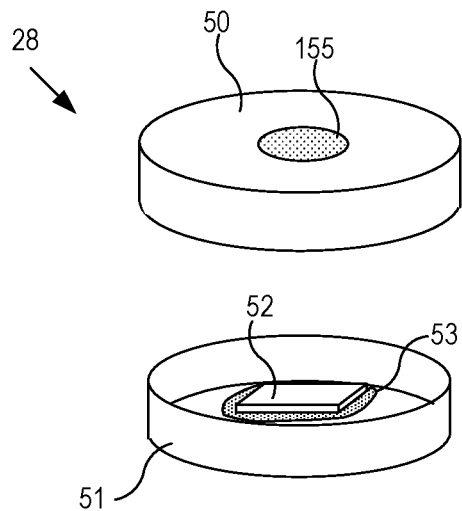
FIG. 5 shows an integrated circuit (IC)-based temperature data logger according to one embodiment of the present invention.

FIG. 5 shows an integrated circuit (IC)-based temperature data logger 28 according to one embodiment of the present invention. As depicted, the data logger 28 includes: a top cover 50; a bottom cover 51; an electrical circuitry 52 for measuring and storing the temperature data; and a securing element 53 that secures the electrical circuitry 52 to the bottom cover 51. When the data logger 28 is assembled, the top and bottom covers 50 and 51 form a housing and the electrical circuitry 52 is disposed in the inner space of the housing. In embodiments, the top and bottom covers 50 and 51 may provide water-proof sealing against fluid.

In embodiments, the top and bottom covers 50 and 51 may be formed of electrically conducting material and operate as two electrodes that are electrically connected to the electrical circuitry 52. For instance, a suitable electrical device may communicate the data logged in the data logger 28 through the top and bottom covers 50 and 51. The top and bottom covers 50 and 51 are formed of material having high thermal conductivity, such as metal, so that the lag between the temperature of the autoclave chamber and the temperature inside the covers 50 and 51 is minimized. The securing element 53 is formed of material having a high thermal conductivity, such as heat conducting glue, to minimize the thermal lag between the temperature inside the covers 50 and 51 and the temperature inside the covers.

Unlike the conventional temperature loggers, a portion 155 of the top cover 50 is directly exposed to the ambient gas via the through hole 18 without damaging the electric circuitry 52 during operation. Likewise, a portion of the bottom cover 51 is directly exposed to the ambient gas via the through hole 32 during operation. This feature allows the data logger 28 to have minimal temperature lag, i.e., the data logger 28 can track the ambient gas temperature more accurately.

Figure 6:
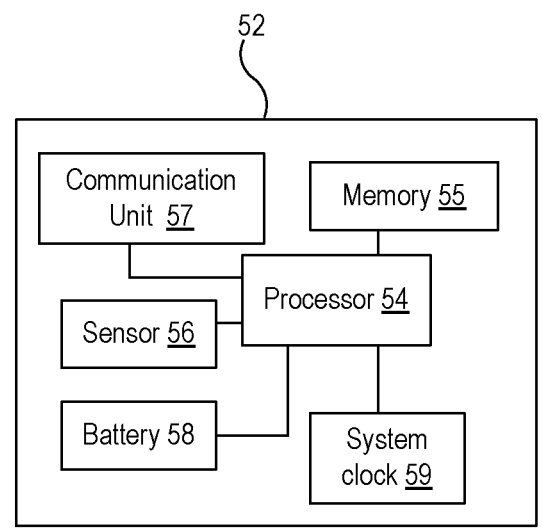
FIG. 6 shows a schematic diagram of an electric circuitry of the IC-based temperature data logger in FIG. 5 according to one embodiment of the present invention.

FIG. 6 shows a schematic diagram of the electronic circuitry 52 of the IC-based temperature data logger 28 in FIG. 5 according to one embodiment of the present invention. In embodiments, the electrical circuitry 52 may be an application-specific integrated circuit (ASIC) and include: a processor 54 for operating various components of the circuitry 52; a sensor 56 for measuring temperature; a battery 58 for providing electrical power to the circuitry 52; a communication unit 57 for communicating data to an external device; a memory 55 for storing the measured temperature data; and a system clock 59 for generating clock signals for the circuitry 52. It is noted that, depending on the application, the circuitry 52 may include additional components, such as additional sensors, and one or more of the components of the circuitry 52 may be omitted.

In embodiments, the processor 54 may be programmed to measure the temperature inside the data logger 28 at a preset time and/or repeat measurements at a preset time interval. In embodiments, the processor 54 may receive the clock signals from the system clock 59 and cause the sensor 56, such as digital temperature sensor, to measure the temperature as scheduled. Then, the processor 54 may store the data into the memory 55, where the memory 55 may be a static RAM, for instance. In embodiments, to minimize the power consumption, the processor 54 may wake up at the scheduled time to measure the temperature and goes back to sleep mode after measurement is completed.

Figure 7:
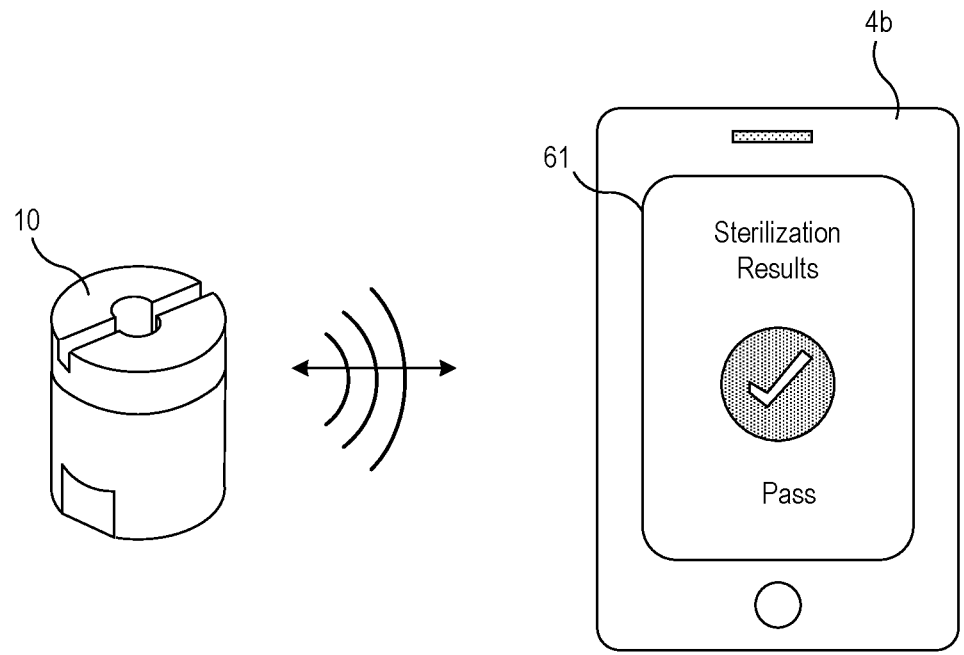
FIG. 7 shows a data communication between a package and a mobile device according to one embodiment of the present invention.

In embodiments, the processor 54 may communicate the stored data to an external device through the communication device 57 and/or the processor 54 may be controlled/programmed through the communication device 57. In embodiments, the communication unit 57 may be a wireless communication device. FIG. 7 shows a data communication between the package 10 (or 7a) and a mobile device 4b according to one embodiment of the present invention.

In embodiments, the user may install an application on the mobile device 4b so that the user can set up the parameters on the circuitry 52, such as time and frequency of data sampling, before the package 10 is mounted in the autoclave. After a sterilization cycle(s), the user may retrieve the stored data from the package 10 using the mobile device 4b and a suitable application may display the temperature data on the display 61 of the mobile device 4b. It is noted that the user may control and communicate to the package 10 using other suitable external devices. For instance, in embodiments, the user may use a computer/server in place of the mobile device 4b. It is noted that one or more of the mobile devices 4, data logger 7b, 7c, and computers 5a, 5b may include a software that archives the records automatically and/or digitally sign the records to ensure tamper proof as a superior record keeping means versus manual paper record keeping. It is also noted that one or more of the mobile devices 4, data logger 7b, 7c, and computers 5a, 5b may detect sterilization failure and provide instant notification of the failure to the user via email or text from the server/cloud.

Figure 8:
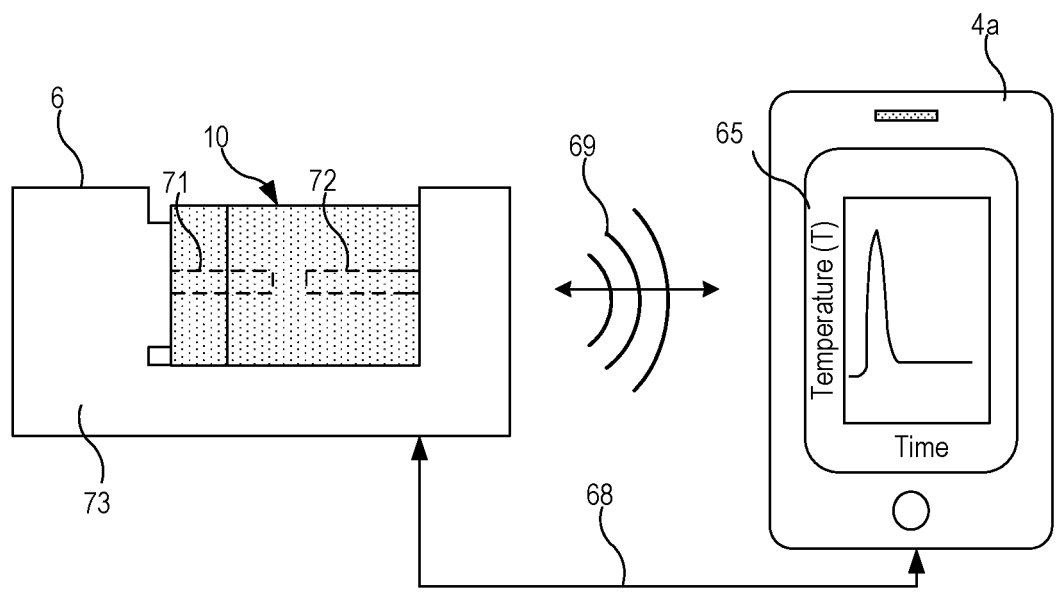
FIG. 8 shows a data communication between a package and a mobile device according to one embodiment of the present invention.

FIG. 8 shows a data communication between the package 10 (or 7b) and a mobile device 4a according to one embodiment of the present invention. As depicted, the package 10 may be docked in a reader 6 that can retrieve data stored in the package 10 and send the retrieved data to the mobile device 4a. In embodiments, the reader 6 has a body 73 and two spring-loaded electrodes 71 and 72 that make electrical contact to the top and bottom surfaces of the data logger 28, respectively, and extract the data stored in the package 10. Also, in embodiments, the reader 6 is used to transmit electrical signals from the mobile device 4a to the package 10 so that the user can program the electrical circuitry 52.

After a sterilization cycle(s), the user may retrieve the stored data from the package 10 using the mobile device 4a and a suitable application displays the temperature data on the display 65 of the mobile device 4a. It is noted that the use may control and communicate to the package 10 using other suitable electrical device. For instance, in embodiments, the user may use a computer/server (e.g. 5a) in place of the mobile device 4a. In some embodiments, the reader 6 exchanges electrical signals with the mobile device 4a through wireless communication 69 or through wire 68, such as universal serial bus (USB) connection.

Figure 9:
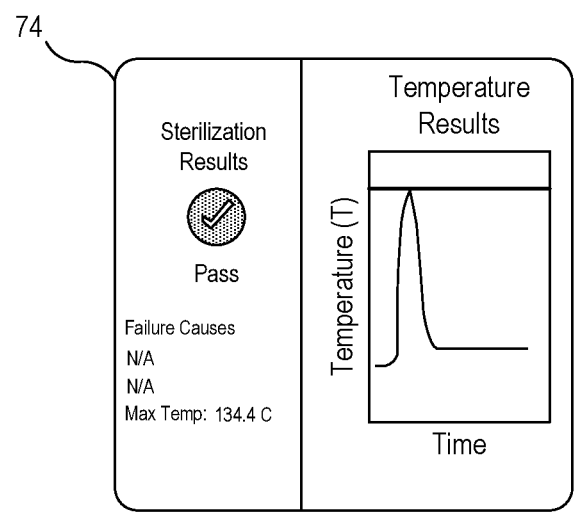
FIG. 9 shows an image displayed on a device according to one embodiment of the present invention.

FIG. 9 shows an image 74 displayed on a device according to one embodiment of the present invention. In embodiments, the device may be any suitable computing device, such as mobile devices 4a-4b or computers/servers 5a-5b, that has a software program, such as web based application, for processing the temperature data retrieved from the package 10 (or, data loggers 7a-7c) and a display for displaying the image 72 for a user.

In embodiments, the device may analyze the temperature data and decide whether the preset sterilization parameters are reached to achieve proper sterilization. Then, as shown in the image 74, the device may display the sterilization result, such as pass or fail, of the sterilization cycle. In embodiments, the image 74 may also include a plot of temperature as a function of time.

In embodiments, one or more computing system may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation phones, laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 1:
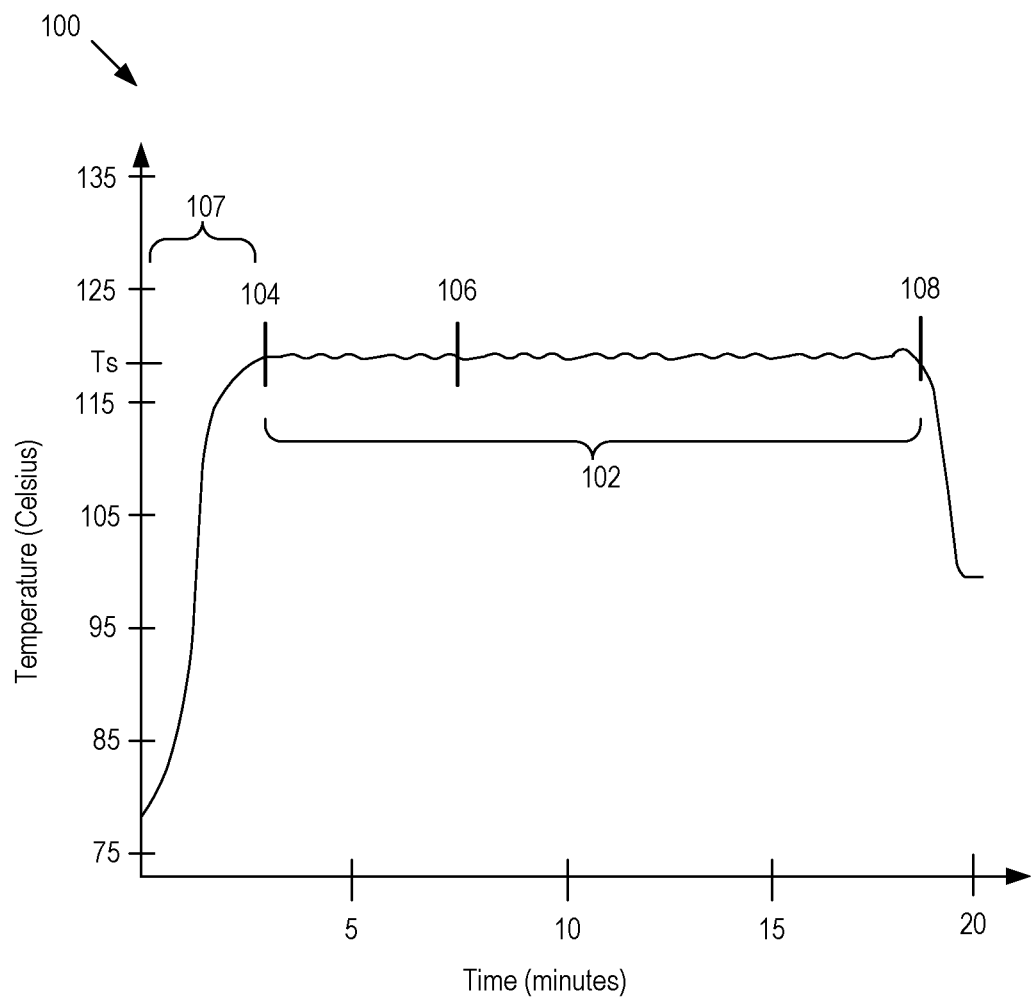
FIG. 1 shows an exemplary plot of temperature during a sterilization cycle.
Figure 10:
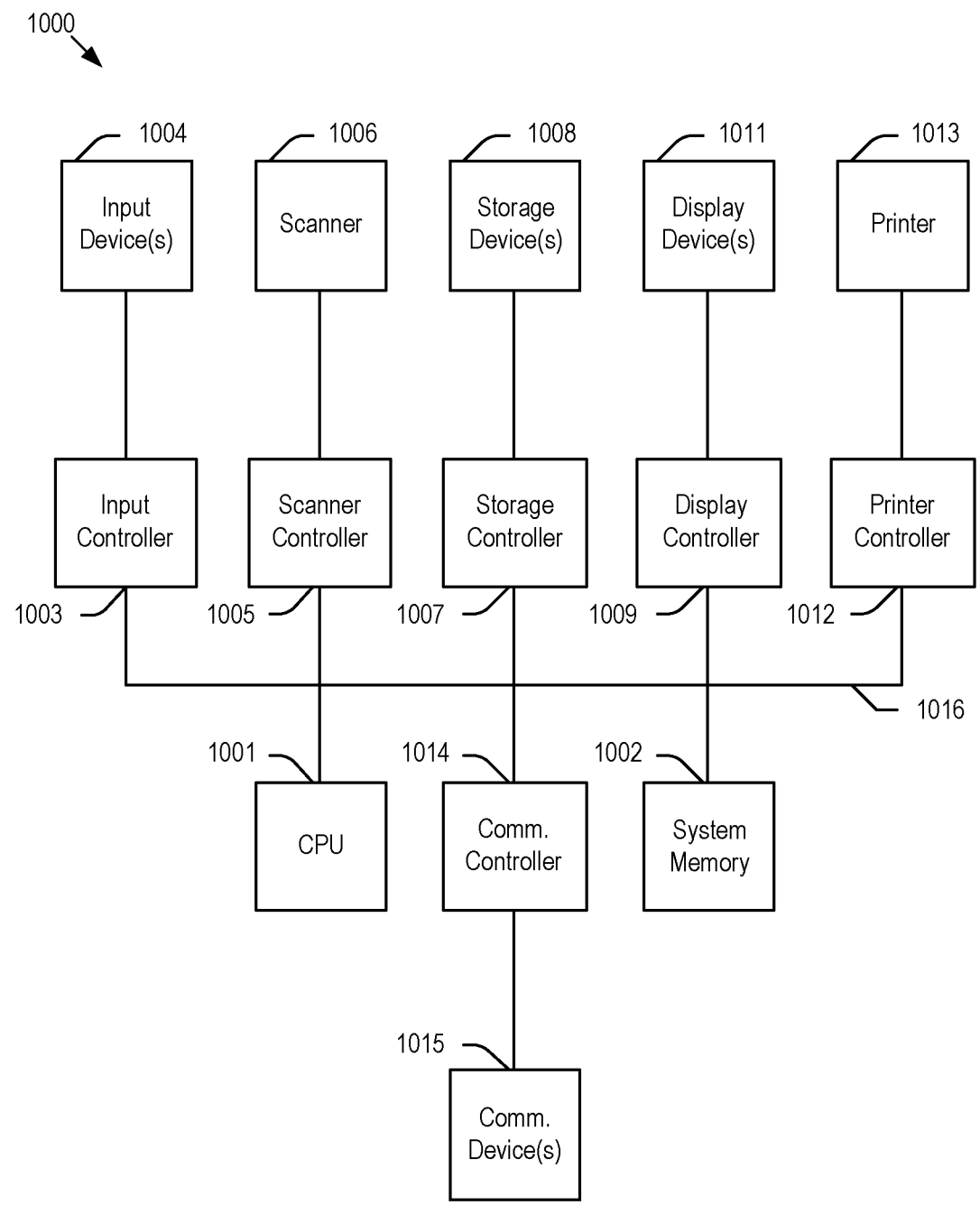
FIG. 10 shows a computer system according to embodiments of the present invention.

Having described the details of the disclosure, an exemplary system 1000, which may be used to implement one or more aspects of the present disclosure, such as mobile devices 4, computers 5, and readers 6, will now be described with reference to FIG. 10. Each client/server in FIG. 1 includes one or more components in the system 1000. As illustrated in FIG. 10, system 1000 includes a central processing unit (CPU) 1001 that provides computing resources and controls the computer. CPU 1001 may be implemented with a microprocessor or the like, and may also include a graphics processor and/or a floating point coprocessor for mathematical computations. System 1000 may also include a system memory 1002, which may be in the form of random-access memory (RAM) and read-only memory (ROM).

A number of controllers and peripheral devices may also be provided, as shown in FIG. 10. An input controller 1003 represents an interface to various input device(s) 1004, such as a keyboard, mouse, or stylus. There may also be a scanner controller 1005, which communicates with a scanner 1006. System 1000 may also include a storage controller 1007 for interfacing with one or more storage devices 1008 each of which includes a storage medium such as magnetic tape or disk, or an optical medium that might be used to record programs of instructions for operating systems, utilities and applications which may include embodiments of programs that implement various aspects of the present disclosure. Storage device(s) 1008 may also be used to store processed data or data to be processed in accordance with the disclosure. System 1000 may also include a display controller 1009 for providing an interface to a display device 1011, which may be a cathode ray tube (CRT), a thin film transistor (TFT) display, or other type of display. System 1000 may also include a printer controller 1012 for communicating with a printer 1013. A communications controller 1014 may interface with one or more communication devices 1015, which enables system 1000 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 1016, which may represent more than one physical bus. However, various system components may or may not be in physical proximity to one another. For example, input data and/or output data may be remotely transmitted from one physical location to another. In addition, programs that implement various aspects of this disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A device for communicating data with a data logger, comprising:
    a body for mounting a data logger thereon, wherein the data logger is disposed inside a capsule, the data logger includes top and bottom covers that define an enclosed space and includes an electrical circuit disposed in the enclosed space and having a memory for storing data;
    a pair of electrodes for extending through two holes formed in the capsule and contacting the top and bottom covers of the data logger, respectively;
    a processor for retrieving data stored in the memory through the pair of electrodes; and
    a communication device for transmitting the data.

2. The device of claim 1, wherein the communication device is a wireless communication device.

3. The device of claim 1, wherein the communication device transmits the data via a wire.

4. The device of claim 1, wherein the communication device transmits an electrical signal received from an external device to the electrical circuit and wherein the electrical signal is used to program the electrical circuit.

5. The device of claim 1, wherein the communication device transmits the data to an external device and the external device includes at least one of a mobile device and a computing device.

6. The device of claim 5, wherein the external device transmits the data transmitted by the communication device to a storage via a network.

7. The device of claim 1, wherein the communication device transmits the data to a data storage via a network.

8. The device of claim 1, wherein the top and bottom covers are formed of electrically conducting material and electrically coupled to the electrical circuit.

9. The device of claim 1, wherein the capsule is formed of electrically insulating material.

10. The device of claim 1, wherein the capsule includes a plug and a base securely coupled to the plug and wherein the two holes are formed in the plug and base, respectively.

11. The device of claim 10, wherein the capsule includes a first o-ring disposed between the plug and the top cover and a second o-ring disposed between the base and the bottom cover and where the first and second o-rings prevent ingress of ambient gas into the data logger.

12. The device of claim 9, wherein the electrical circuit includes a sensor for measuring a temperature of ambient gas around the data logger and the data includes information of the temperature measured by the sensor.

13. A system for communicating data with a data logger, comprising:
   at least one processor; and
   a communication device that is communicatively coupled to the at least one processor and receives data from a data logger, wherein the data logger is disposed inside a capsule that prevents ingress of atmospheric gas into the data logger, the data logger includes top and bottom covers that define an enclosed space and includes an electrical circuit disposed in the enclosed space and having a memory for storing the data.

14. The system of claim 13, wherein the communication device is a wireless communication device and communicates the data with a communication unit included in the electrical circuit of the data logger.

15. The system of claim 14, wherein the communication device transmits an electrical signal to the communication unit and wherein the electrical signal is used to program the electrical circuit of the data logger.

16. The system of claim 14, wherein the communication device communicates with the communication unit via a reader, wherein the reader includes:
   a body for mounting the data logger thereon;
   a pair of electrodes for extending through two holes formed in the capsule and contacting the top and bottom covers of the data logger, respectively;
   a processor for retrieving the data stored in the memory through the pair of electrodes; and
   a communication device for transmitting the data.

17. The system of claim 13, further comprising: a display communicatively coupled to the at least one processor and for rendering an information related to the data.

18. The system of claim 13, wherein the electrical circuit includes a sensor for measuring a temperature of the ambient gas and the data includes information of the temperature measured by the sensor.

19. The system of claim 13, wherein the communication device communicates the data with a data storage via a network.

20. The system of claim 13, wherein the system is a mobile device.

* * * * *